US012622583B2

(12) United States Patent
Nimtsovitch

(10) Patent No.: US 12,622,583 B2
(45) Date of Patent: May 12, 2026

(54) AUTOMATED AUDIO-FEEDBACK COMPUTERIZED SYSTEM AND METHOD FOR ARTIFICIAL INTELLIGENCE (AI)-CONTROLLED EYE EXERCISE

(71) Applicant: DIPLO D LTD, Netanya (IL)

(72) Inventor: Claude Nimtsovitch, Netanya (IL)

( * ) Notice: Subject to any disclaimer, the term of this patent is extended or adjusted under 35 U.S.C. 154(b) by 957 days.

(21) Appl. No.: 17/765,001

(22) PCT Filed: May 10, 2021

(86) PCT No.: PCT/IL2021/050530
§ 371 (c)(1),
(2) Date: Nov. 17, 2022

(87) PCT Pub. No.: WO2022/238986
PCT Pub. Date: Nov. 17, 2022

(65) Prior Publication Data
US 2024/0065546 A1     Feb. 29, 2024

(51) Int. Cl.
| | |
|---|---|
| *A61B 3/113* | (2006.01) |
| *A61B 3/00* | (2006.01) |
| *A61B 3/024* | (2006.01) |
| *A61B 3/08* | (2006.01) |
| *A61B 3/10* | (2006.01) |
| *A61B 3/12* | (2006.01) |
| *A61H 5/00* | (2006.01) |

(52) U.S. Cl.
CPC ............... *A61B 3/113* (2013.01); *A61B 3/08* (2013.01); *A61H 5/005* (2013.01)

(58) Field of Classification Search
CPC ........... A61B 3/02; A61B 3/113; A61B 3/102; A61B 3/1015; A61B 3/1225; A61B 3/024; A61B 3/005
USPC ....... 351/209, 200, 205, 206, 210, 221–223, 351/245–246
See application file for complete search history.

(56) References Cited

U.S. PATENT DOCUMENTS

| | | | | |
|---|---|---|---|---|
| 11,238,340 B1 * | 2/2022 | Anderson | ................ | G06N 3/02 |
| 2011/0299034 A1 * | 12/2011 | Walsh | .................... | A61B 3/132 |
| | | | | 351/206 |
| 2015/0035744 A1 * | 2/2015 | Robbins | ............... | G02B 27/017 |
| | | | | 345/156 |
| 2016/0128892 A1 * | 5/2016 | Nimtsovitch | ............ | A61H 5/00 |
| | | | | 601/37 |
| 2020/0372632 A1 * | 11/2020 | Chauhan | .............. | A61B 3/0025 |
| 2021/0290053 A1 * | 9/2021 | Tran | .................... | G02B 27/0093 |
| 2022/0224843 A1 * | 7/2022 | Adamousky | ........... | A61B 3/005 |

* cited by examiner

*Primary Examiner* — Dawayne Pinkney
(74) *Attorney, Agent, or Firm* — Daniel J. Swirsky; AlphaPatent Associates Ltd.

(57) ABSTRACT

The present invention provides a computerized operator-controlled optical system and method for tracking eye exercises of a patient, the system including an optical tracking device adapted to allow an operator to track eye exercises of a patient, a patient-activated apparatus for performing eye exercises of binocular vision and a processor adapted to receive data from the optical tracking device and from the patient-activated apparatus thereby providing the operator with at least one indication of the eye exercises of the patient over time.

20 Claims, 14 Drawing Sheets

150

152

160

170

172

602 600

604 110 120 130

620

900
302
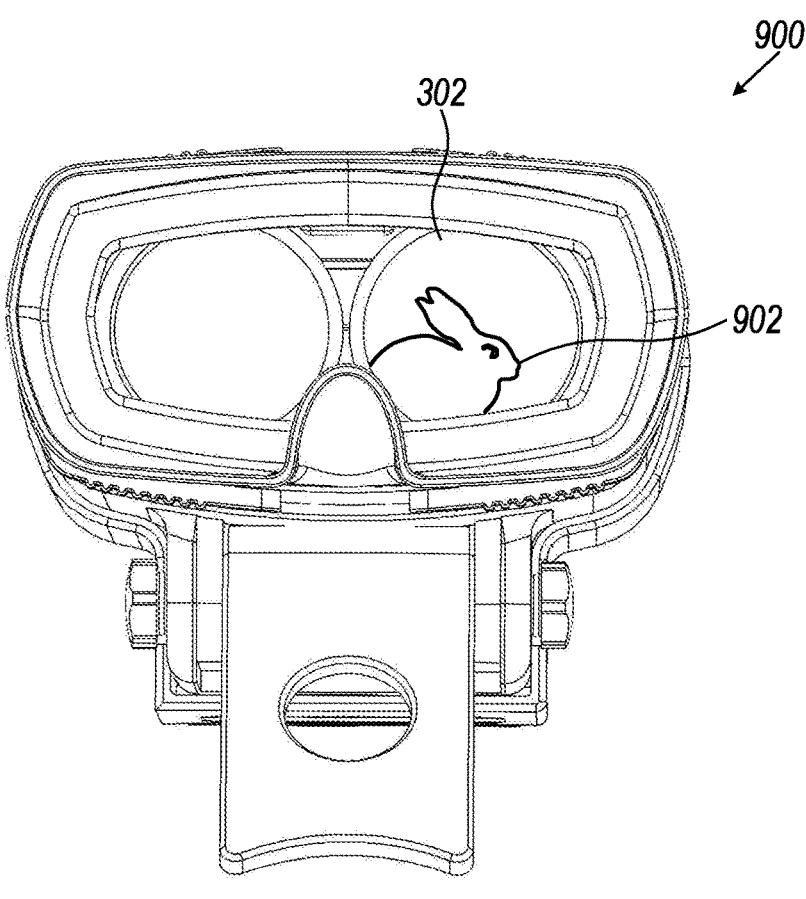
902
FIG. 9
FIG. 10
1000
1006
1002
304
1004
1008
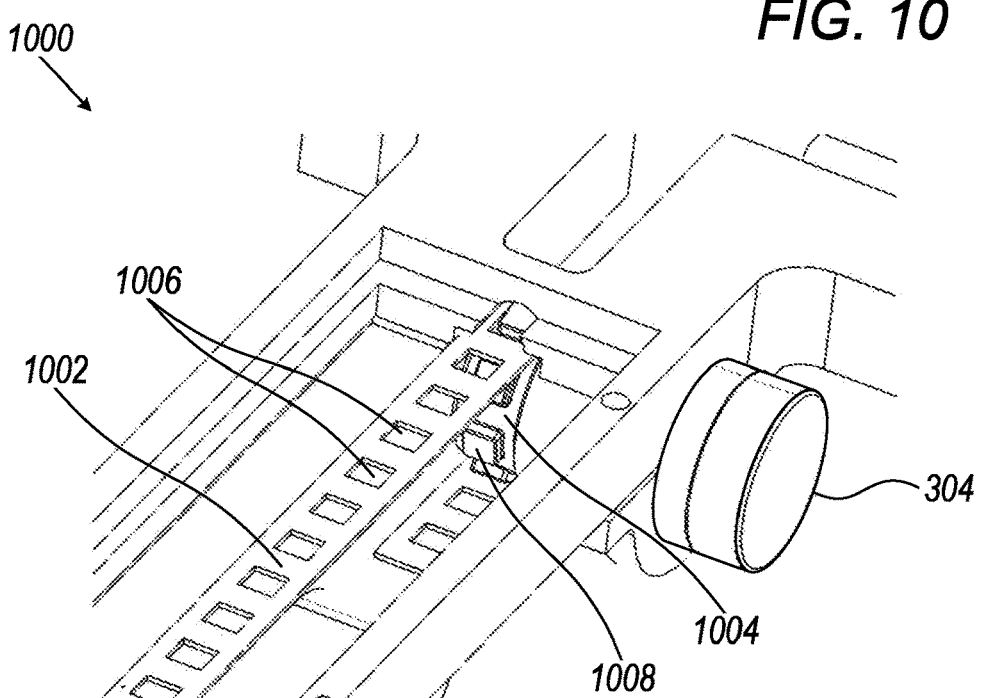

AUTOMATED AUDIO-FEEDBACK COMPUTERIZED SYSTEM AND METHOD FOR ARTIFICIAL INTELLIGENCE (AI)-CONTROLLED EYE EXERCISE

FIELD OF THE INVENTION

The present invention relates generally to systems and methods for improving eye activities, and more specifically to automated operator-controlled methods and apparatus for improving eye activities.

BACKGROUND OF THE INVENTION

Many prior art devices have been developed to assist a person with eye focus defects to perform orthoptic eye exercises. These exercises are adapted to correct mainly fusion deficiencies, such as, but not limited to convergence insufficiency, divergence excess or intermittent strabismus. Convergence insufficiencies include exophoria or esophoria. Intermittent strabismus includes intermittent exotropia and esotropia. These prior systems currently in use are based on the stereoscopic effect or binocular vision, wherein each eye is presented a separate picture, and the patient is required to exert the eyes muscles to integrate the two pictures into one focused image.

Moreover, these prior art devices are not useful for the intermittent suppression deficiency, that is while one eye ceases at times from participating in the image forming process. When this happens, the usual eye exercises are no more effective.

In prior art Israel Patent No. 119274, the present inventor disclosed a device which can be used at home. However, the picture movement is made manually by the user himself. Sometimes the velocity of movement is not appropriate for the desired exercise. There may not be sufficient consistency in the exercise, when performing it at a different rate each time.

Moreover, the user has no indication, while performing the exercise, of the actual performance having been achieved. Only after finishing the exercise, the user can look at the achieved performance; this may not be enough an incentive for improvement, nor does it give an intuitive feeling for what is done, in real time.

Yet another possible problem in prior art is that the user is responsible for deciding when picture tracking is lost—this is important in evaluating the success of the exercise, as well as motivating the user. However, the non-professional user may not be aware of his losing track, or may become aware of it only after a time delay—thus the effectiveness of the device may be impaired.

WO2009/138964 to Nimstovitch describes an optical apparatus for performing eye exercise comprising base means shaped generally like an elongated beam; picture means which is suitable for eye exercise and includes positioning means for positioning said picture means at various locations along said base means; electrical light means attached to said base means, including lamp means and switch means for turning said lamp on and off; ocular means including two viewing apertures, each located in front of one eye, said ocular means being mounted on or close to one end of said base means; audio feedback means for generating, during the eye exercise performance, an audio signal whose characteristics are indicative of the distance of the moving picture from the user's eyes.

WO2014199366A1 to Nimstovitch describes a computerized operator-controlled optical system and method for tracking eye exercises of a patient, the system including an optical tracking device adapted to allow an operator to track eye exercises of a patient, a patient-activated apparatus for performing eye exercises of binocular vision and a processor adapted to receive data from the optical tracking device and from the patient-activated apparatus thereby providing the operator with at least one indication of the eye exercises of the patient over time.

None of the prior art devices are standalone nor automatically activated, without requiring a professional operator, such as an optician, a physician or a technician to track the user or patient's progress and to compare his/her progress over time. There thus remains a need to provide improved standalone automated orthoptic devices and methods.

SUMMARY OF THE INVENTION

It is an object of some aspects of the present invention to provide an automated AI-controlled optical system and method for tracking eye exercises of a user or patient, the system including a user-activated apparatus for performing eye exercises of both eyes together and an AI-controlled optical tracking device for track user eye movement thereby providing the user with eye exercises for improving user eye function over time.

The invention further provides a standalone compact, foldable, automated AI-controlled optical system, which is around 20 cm in length, when folded. The system is controlled by software, which is configured to enable a user to use it unattended.

The software is further configured to provide the user with audible real-time instructions. These instructions include verbal instructions for straining and for relaxing an eye or both eyes.

According to further embodiments of the present invention, the automated AI-controlled optical system further provides audible sounds which vary according to the different levels of exercise.

According to further embodiments of the present invention, the automated AI-controlled optical system is further constructed and configured to perform eyesight tests and depth sight tests.

This invention further relates to an automated orthoptic eye exercise device having two fixation centers and using AI-controlled audio feedback.

According to the present invention, there is provided an automated optical device for performing orthoptic eye exercise at a user's/patient's home.

According to one aspect of the present invention, the device includes two fixation centers screens, each located on the axis of symmetry between the eyes, each screen adapted to display an image or images, used for eye exercise.

The patient can choose to look at screen at a time, with the other screen appearing double.

The two screens are adapted to display any image, letter, number or item, adapted for understanding by the user, by age, literacy, eyesight etc.

The eye exercise device may include a trial frame, whose distance between the two eyes is adjustable, with replaceable optical accessories. The replaceable optical accessories may include lenses and/or prisms.

The distance to the first and second screen is adjustable. The eye exercise device includes two lights, each included in one fixation center, with means for the activation of each light. According to a seventh aspect of the present invention, the device further includes colored filters for eye exercise purposes.

Furthermore, the invention includes a geared members for moving the closer screen towards the user's eyes at a controlled speed, to achieve a consistent framework for eye exercising.

The invention also includes audio feedback means for indicating to the user, in real time, the measure of closeness of the screen to the eyes, that is the index of user's achievement in the present exercise.

Moreover, the eyes tracking performance is continuously automatically recorded by the AI-controlled optical system such that loss of tracking by the user's eye or eye is automatically detected, to achieve a more reliable index.

Further objects, advantages and other features of the present invention will become obvious to those skilled in the art upon reading the disclosure set forth hereinafter.

There is thus provided according to an embodiment of the present invention, an automated audio feedback computerized AI-controlled optical system for tracking eye exercises of a user, the system including;

a. an automated optical tracking device to track eye exercises of the user;

b. a user-activated apparatus for performing eye exercises of two eyes together; and c. a processor adapted to receive data from the optical tracking device and from the user-activated apparatus thereby providing at least one indication of the eye exercises of the user over time.

Additionally, according to an embodiment of the present invention, the optical system further includes software for downloading data to a memory in the system, the data being associated with the user and the eye exercises performed by the user.

Furthermore, according to an embodiment of the present invention, the optical system further includes software readable by the processor, wherein the software is adapted to form user records over time.

Moreover, according to an embodiment of the present invention, the automated optical tracking device incudes a camera.

Additionally, according to an embodiment of the present invention, the automated optical tracking device is a video camera.

Further, according to an embodiment of the present invention, the camera is adapted to capture images of each the patient's eyes of semi-continuously or continuously during use of the system by the user.

Moreover, according to an embodiment of the present invention, the software is adapted to output patient records to an external computer system.

Additionally, according to an embodiment of the present invention, the system is constructed and configured to improve eye fusion deficiencies of the patient over time.

Furthermore, according to an embodiment of the present invention, the fusion deficiencies, are selected from convergence insufficiency, divergence excess, intermittent strabismus and combinations thereof.

Additionally, according to an embodiment of the present invention, the convergence insufficiencies are selected from exophoria and intermittent exotropia.

Moreover, according to an embodiment of the present invention, the intermittent strabismus is intermittent exotropia.

Additionally, according to an embodiment of the present invention, the at least one screen is configured to display at least one of an image, a video, a picture, a photo, an alphanumeric symbol, a three dimensional (3D) item and at least one red colored shape.

Moreover, according to an embodiment of the present invention, the user-activated apparatus further includes an audio feedback element for generating, during the eye exercises, an audio signal whose characteristics are indicative of a distance of one of the at least two screens from the at least one viewing aperture.

Additionally, according to an embodiment of the present invention, the carrier element further includes a distance adjusting element adapted to position the at least one screen at a distance from the at least one viewing aperture.

Yet further, according to an embodiment of the present invention, a computerized operator-controlled optical system further including a remote controlled motor for moving the at least one screen towards the at least one viewing aperture.

Additionally, according to an embodiment of the present invention, the audio feedback signal's characteristics include its frequency.

Further, according to an embodiment of the present invention, the audio feedback signal includes pulses and the signal's characteristics include its pulse repetition rate.

Furthermore, according to an embodiment of the present invention, the signal's characteristics further include the signal's frequency.

There is thus provided according to an additional embodiment of the present invention, an automated audio feedback computerized AI-controlled optical method for tracking eye exercises of a user, the method including;

a. performing eye exercises of both the user's eyes together to form a patient data output; and b. processing the user data output over time thereby providing at least one indication of the eye exercises of the user over time.

Additionally, according to an embodiment of the present invention, the method further includes storing the user data output and the operator data output over time in at least one of a computer memory and a memory card.

Moreover, according to an embodiment of the present invention, the method further includes tracking a reduction in eye fusion deficiencies of the user over time.

EMBODIMENTS

1. An automated audio-feedback AI-controlled optical system for tracking eye exercises of a patient, the system comprising:
    a) an AI-controlled optical tracking device adapted to track eye exercises of a patient;
    b) a user-activated apparatus for performing eye exercises of both eyes together; and
    c) a processor adapted to receive data from the AI-controlled eye tracking device and from the user-activated apparatus thereby providing the user with eye exercises for improving user eye function over time.

2. An automated audio-feedback AI-controlled optical system according to embodiment 1, further comprising an electronic apparatus adapted to download the data to a memory in the system.

3. An automated audio-feedback AI-controlled optical system according to embodiment 1, further comprising software readable by the processor, wherein the software is adapted to form user records over time.

4. An automated AI-controlled optical system according to embodiment 1, wherein the optical tracking device comprises a camera.

5. An automated AI-controlled optical wherein the optical tracking device comprises a video camera.

6. An automated AI-controlled optical system according to embodiment 1, according to embodiment 5, wherein the camera is adapted to capture images of each the users eyes continuously or semi-continuously.

7. An automated AI-controlled optical system according to embodiment 3, wherein the software is adapted to output user records to an external computer system.

8. An automated AI-controlled optical system according to embodiment 1, wherein the system is constructed and configured to improve eye fusion deficiencies of the patient over time.

9. An automated AI-controlled optical system according to embodiment 8, wherein the fusion deficiencies, are selected from convergence insufficiency, divergence excess, intermittent strabismus and combinations thereof.

10. An automated AI-controlled optical system according to embodiment 9, wherein the convergence insufficiencies is exophoria.

11. An automated AI-controlled optical system according to embodiment 9, wherein the intermittent strabismus is intermittent exotropia.

12. An automated AI-controlled optical system according to embodiment 1, wherein the user-activated apparatus comprises:
   a. an ocular apparatus comprising:
      i. at least one viewing aperture, disposed in front of the patient's eyes;
      ii. the viewing aperture adapted to receive at least one of:
         a. an optical lens;
         b. an optical filter; and
         c. a prismatic lens.

13. An automated AI-controlled optical system according to embodiment 12, wherein the user-activated apparatus further comprises:
   a. a carrier element adapted to carry at least one of said two screens towards and away from the ocular apparatus.

14. An automated AI-controlled optical system according to embodiment 13, wherein the two screens display at least one of a picture, a photo, an alphanumeric symbol and at least one colored shape.

15. An automated AI-controlled optical system according to embodiment 12, wherein the user-activated apparatus further comprises:
   a. at least one electrical light element attached to the carrier element.

16. An automated AI-controlled optical system according to embodiment 12, wherein the user-activated apparatus further comprises an audio feedback element for generating, during the eye exercises, an audio signal whose characteristics are indicative of a distance of one of the at least two screens from the at least one viewing aperture.

17. An automated AI-controlled optical system according to embodiment 12, wherein the carrier element further comprises a distance adjusting element adapted to position the at least two screens and the lamp means each at an equal distance from the at least one viewing aperture.

18. An automated AI-controlled optical system according to embodiment 1, further comprising a remote controlled motor for moving at least one of the two screens towards the at least one viewing apertures.

19. An automated AI-controlled optical system according to embodiment 17, wherein the audio feedback signal's characteristics include its frequency.

20. An automated AI-controlled optical system according to embodiment 19, wherein the audio feedback signal includes pulses and the signal's characteristics include its pulse repetition rate.

21. An automated AI-controlled optical system according to embodiment 20, wherein the signal's characteristics further include the signal's frequency.

22. An automated AI-controlled optical method for tracking eye exercises of a patient, the method comprising:
   a. performing eye exercises of both patient's eyes together to form a patient data output;
   b. automated AI-controlled tracking of the eye exercises of the user to form user output data; and
   c. processing the user output data over time thereby providing at least one indication of the eye exercises of the patient over time.

23. An automated AI-controlled optical method according to embodiment 22, further comprising storing the user data output and the operator data output over time in a computer memory.

24. An automated AI-controlled optical method according to embodiment 23, further comprising tracking a reduction in eye fusion deficiencies of the user over time.

25. An automated AI-controlled optical method according to embodiment 24, wherein the fusion deficiencies, are selected from convergence insufficiency, divergence excess, intermittent strabismus and combinations thereof.

26. An automated AI-controlled optical method according to embodiment 25, wherein the convergence insufficiencies are selected from exophoria and esophoria.

27. An automated AI-controlled optical method according to embodiment 25, wherein the intermittent strabismus is selected from intermittent exotropia and intermittent esotropia.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIG. 9 is a simplified schematic illustration showing a perspective front view of an opened third section of the automated AI-controlled optical system of FIG. 1A, in accordance with an embodiment of the present invention;

FIG. 10 is a simplified schematic illustration showing details of a stepper motor and inner moving rail of the automated AI-controlled optical system of FIG. 1A, in accordance with an embodiment of the present invention;

In all the figures similar reference numerals identify similar parts.

DETAILED DESCRIPTION OF THE EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

Figure 1A:
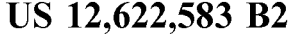
FIG. 1A is a simplified schematic illustration showing a perspective view of an opened automated AI-controlled optical system for tracking eye exercises of a user, in accordance with an embodiment of the present invention.

FIG. 1A is a simplified schematic illustration showing a perspective view of an opened automated AI-controlled optical system 100 for tracking eye exercises of a user, in accordance with an embodiment of the present invention. System 100 comprises an eye piece section 110, a middle section 120 and a rear section 130. The eyepiece section has two lens holders 102, 104 (as well as lens storage receptacles, not shown) and a nose recess 106 there-between, as well as a polymer head receiving band 108 or rubber sealing member (typically made of rubber) for receiving an upper part of a person's face. The middle section comprises an openable stand 122 and a knob 124 for adjusting a tilt of the stand. The eye piece section further comprises a casing 126 with a receiving element 121 for receiving extension teeth 114 on a casing 112 of the eye piece section, to extend or nest it.

The middle section further comprises a dashed rail 116, configured to be received by a second receiving element 132 on the rear section. The middle section further comprises another dashed rail 128, adapted to be received by the rear section to reduce the system length, or to nest the sections together, in a telescopic manner. Many options for opening and closing the system are possible.

In the current embodiment, the dashed rail and receiving elements act like step wise extendable arms on each side of the system, enabling the eyepiece section to be nested in the middle section, the middle section into the rear section. Thus, the eye piece section has a smaller cross section than the middle piece section and the middle piece section has a smaller cross section than the rear section.

The length in the open mode of the system is around 40 cm, with the aim to provide an effective eye training for convergence, accommodation, and physiological diplopia.

Figure 1B:
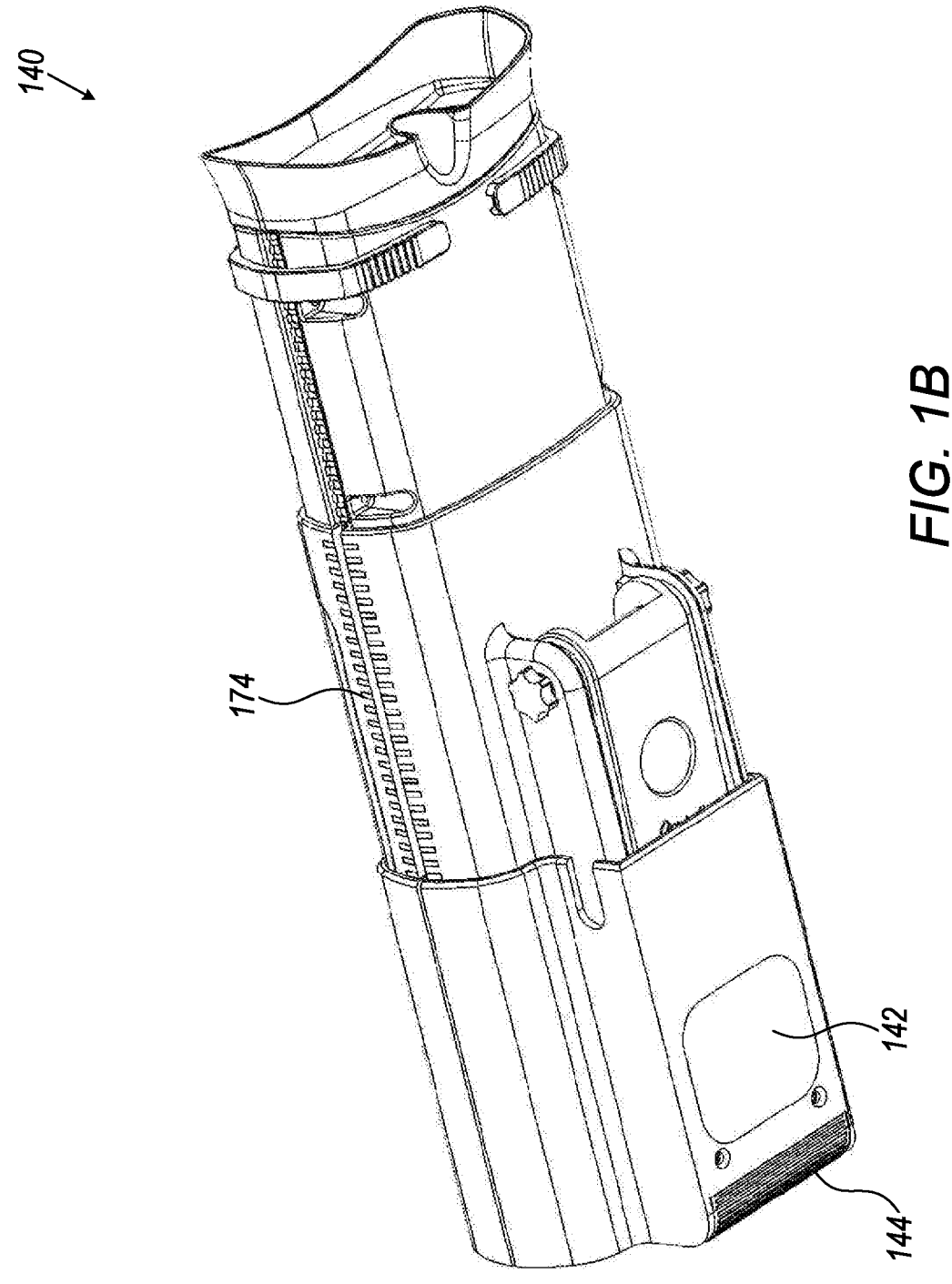
FIG. 1B is a simplified schematic illustration showing a view of a lower side an automated AI-controlled optical system for tracking eye exercises of a user, in accordance with an embodiment of the present invention.

FIG. 1B is a simplified schematic illustration showing a view of a lower side 140 of an automated AI-controlled optical system 100 for tracking eye exercises of a user, in accordance with an embodiment of the present invention.

This illustration shows a rear, anti-slip element 144 disposed on lower side of the rear section, as well as a label receiving element 142. An adjustable foldable front leg shown in the open mode, a bolt for locking the leg in selected angles of use, two locations for informative stickers: the first in the lower side and the second in the back side of the device.

Figure 1C:
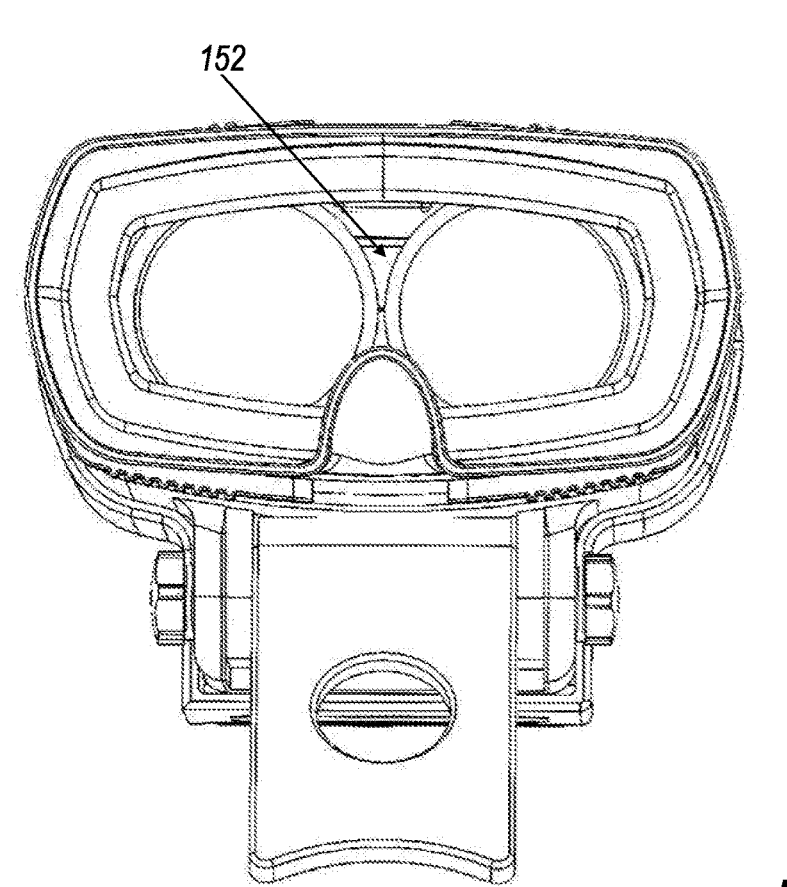
FIG. 1C is a simplified schematic illustration showing a view of a front view of an opened automated AI-controlled optical system for tracking eye exercises of a user, in accordance with an embodiment of the present invention.

FIG. 1C is a simplified schematic illustration showing a view of a front view 150 of an opened automated AI-controlled optical system 100 for tracking eye exercises of a user, in accordance with an embodiment of the present invention; A large window 152 is seen for the user's eyes. In one embodiment, it is in the shape of a diving mask, without separation between the two eyes. This is to optimize the binocular convergence of the user's eyes, when exercising.

Figure 1D:
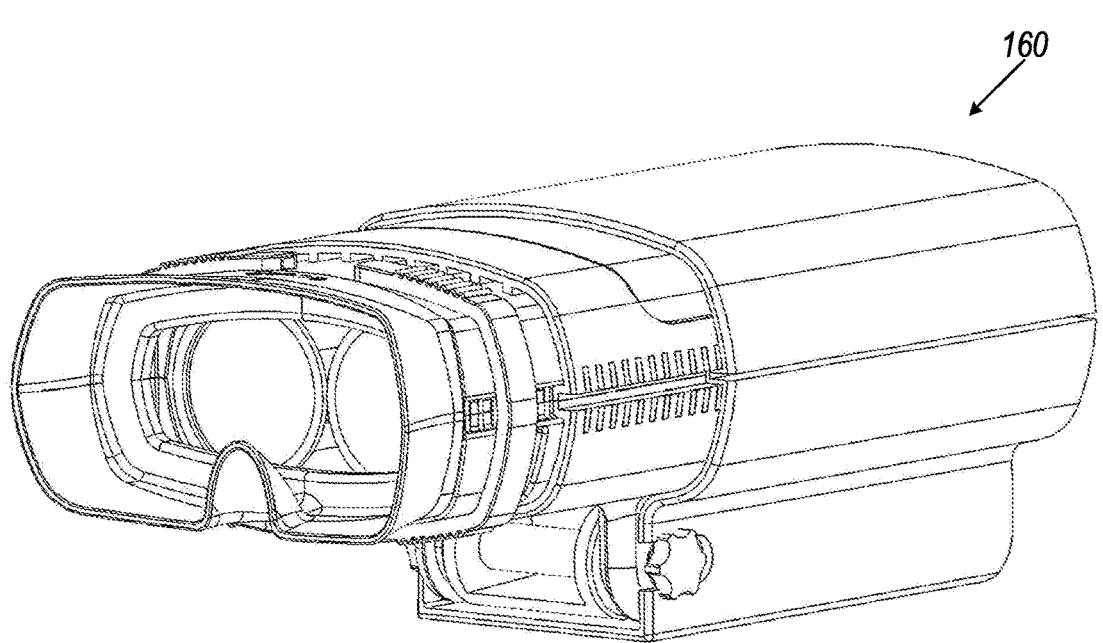
FIG. 1D is a simplified schematic illustration showing a view of a lower side of a partially folded automated AI-controlled optical system for tracking eye exercises of a user, in accordance with an embodiment of the present invention.

FIG. 1D is a simplified schematic illustration showing a view 160 of a lower side of a partially folded automated AI-controlled optical system for tracking eye exercises of a user, in accordance with an embodiment of the present invention; This illustration shows in the middle of the system, an adjustable, foldable front leg, which allows the device to stand at a suitable height in front of the user's eyes.

Figure 1E:
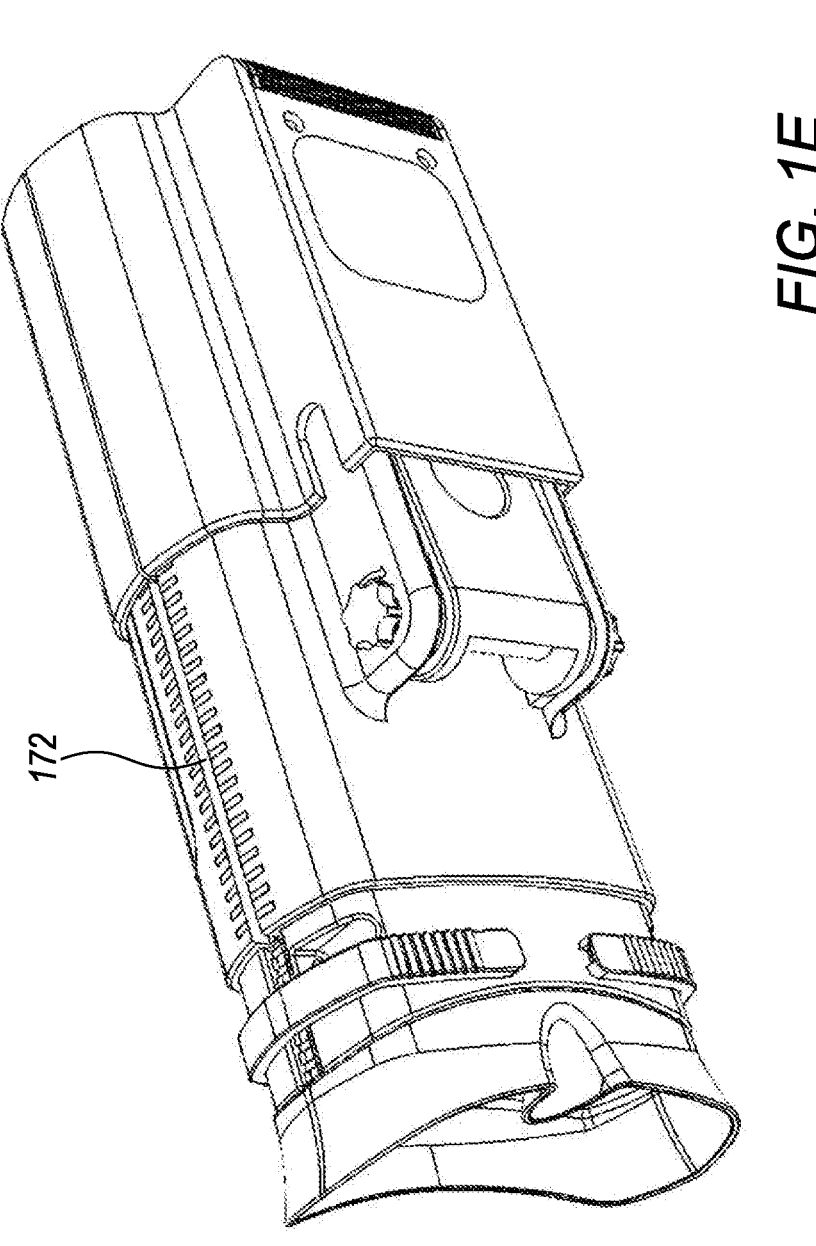
FIG. 1E is a simplified schematic illustration showing a lower side view of a closed automated AI-controlled optical system for tracking eye exercises of a user, in accordance with an embodiment of the present invention.

FIG. 1E is a simplified schematic illustration showing a side view 170 of a closed automated AI-controlled optical system 100 for tracking eye exercises of a user, in accordance with an embodiment of the present invention; In this closed mode, the device has 20 cm length and can be easily stored when not in use.

On the right side are shown inner dotted rails 172 restraining the horizontal opening and closing movement; these rails exist in the left side too 174 (shown in FIG. 1B).

Figures 2A, 2B:
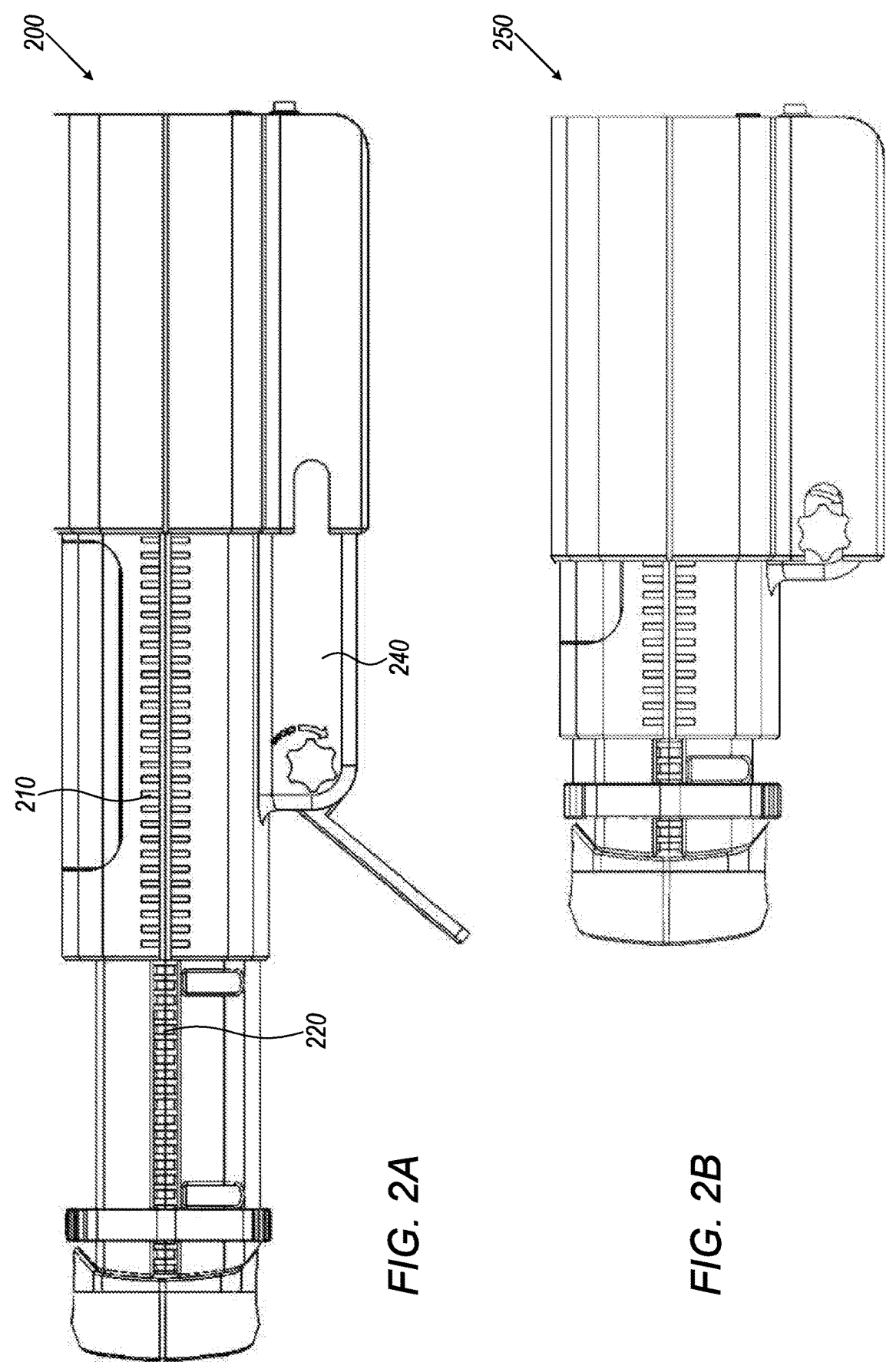
FIG. 2A is a simplified schematic illustration showing a side view of an opened (extended) automated AI-controlled optical system for tracking eye exercises of a user, in accordance with an embodiment of the present invention.
FIG. 2B is a simplified schematic illustration showing a side view of a closed (retracted) automated AI-controlled optical system for tracking eye exercises of a user, in accordance with an embodiment of the present invention.

FIG. 2A is a simplified schematic illustration showing a side view 200 of an opened (extended) automated AI-controlled optical system for tracking eye exercises of a user, in accordance with an embodiment of the present invention.

On each side (here the right side is shown), a dashed rail 220 is localized to restrain the horizontal opening and closing movement of the eyepiece section into the middle section and a second dashed rail 210 on the middle section for being received by the rear section.

Two rail supports are shown: the front rail support and the middle rail support; the back rail support is not shown in FIG. 2A.

The adjustable front stand is shown, with a knob for locking the stand at various selected angles.

FIG. 2B is a simplified schematic illustration showing a side view 250 of a closed (retracted) automated AI-controlled optical system for tracking eye exercises of a user, in accordance with an embodiment of the present invention. The length of the device is halved for easier storage or transport.

The adjustable front stand is folded and stored into its cell 240 shown in FIG. 2A.

Figures 3A, 3B:
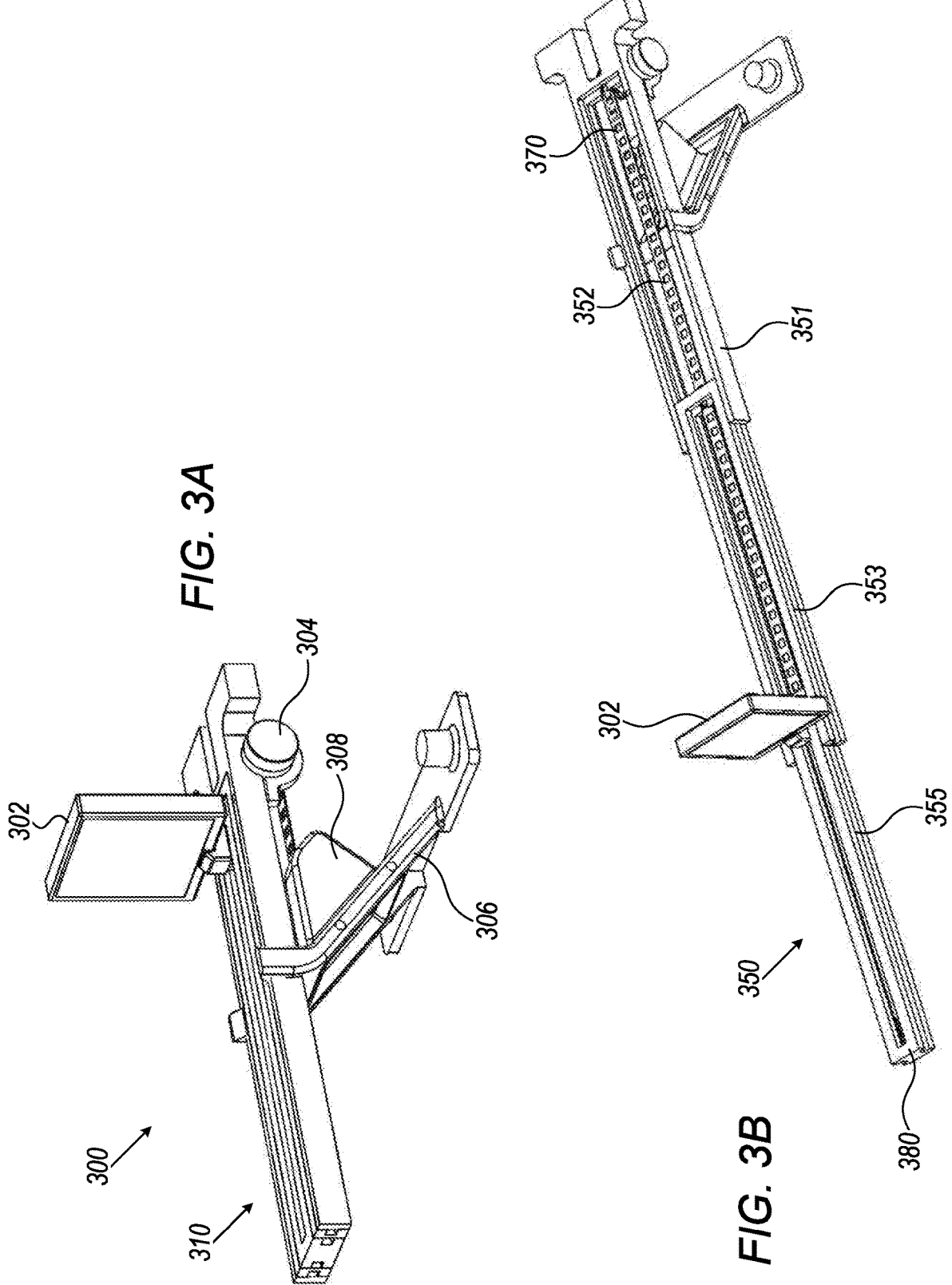
FIG. 3A is a simplified diagram of a screen on a rail of the system of FIG. 1A, in accordance with an embodiment of the present invention.
FIG. 3B is a simplified diagram of an extension rail mechanism of the system of FIG. 1A, in accordance with an embodiment of the present invention.

FIG. 3A is a simplified diagram of a screen on an inner rail apparatus 300 of the system of FIG. 1A, in accordance with an embodiment of the present invention. In this figure the device is in its closed mode. A moving LED screen 302 is disposed on the top of an extendable telescopic 3-step rail element 310 shown in FIG. 3A, which is activated by a stepper motor 304 shown, along the telescopic 3-step rail element. inner rail apparatus 300 further comprises a conveyor bel cartridge 308 and a rail support element 306 (there are further support elements, not seen in the diagram).

FIG. 3B is a simplified diagram of an inside extension rail mechanism 350 of the system of FIG. 1A, in accordance with an embodiment of the present invention.

A metallic spring belt 352 is used to extend or retract the extendable telescopic 3-step rail element 310 of FIG. 3A. One of the three rail supports 306 is shown. The extendable telescopic 3-step rail element 310 comprises a rear rail element 351, a middle rail element 353, and an eyepiece rail element 355. These three elements 351, 353, 355 act as a horizontal "fireman's ladder" with 355 being nested in 353 and 353 being nested into 351.

The moving LED screen 302 is here shown in a nearer location to the front the eye piece section of the system, and the final location of the moving LED screen is at a front end of the rail 380, in the left side of FIG. 3B. The LED screen can also be moved along the extendable telescopic 3-step rail element 310 to a rear end 370 of the rear section.

Figure 4A:
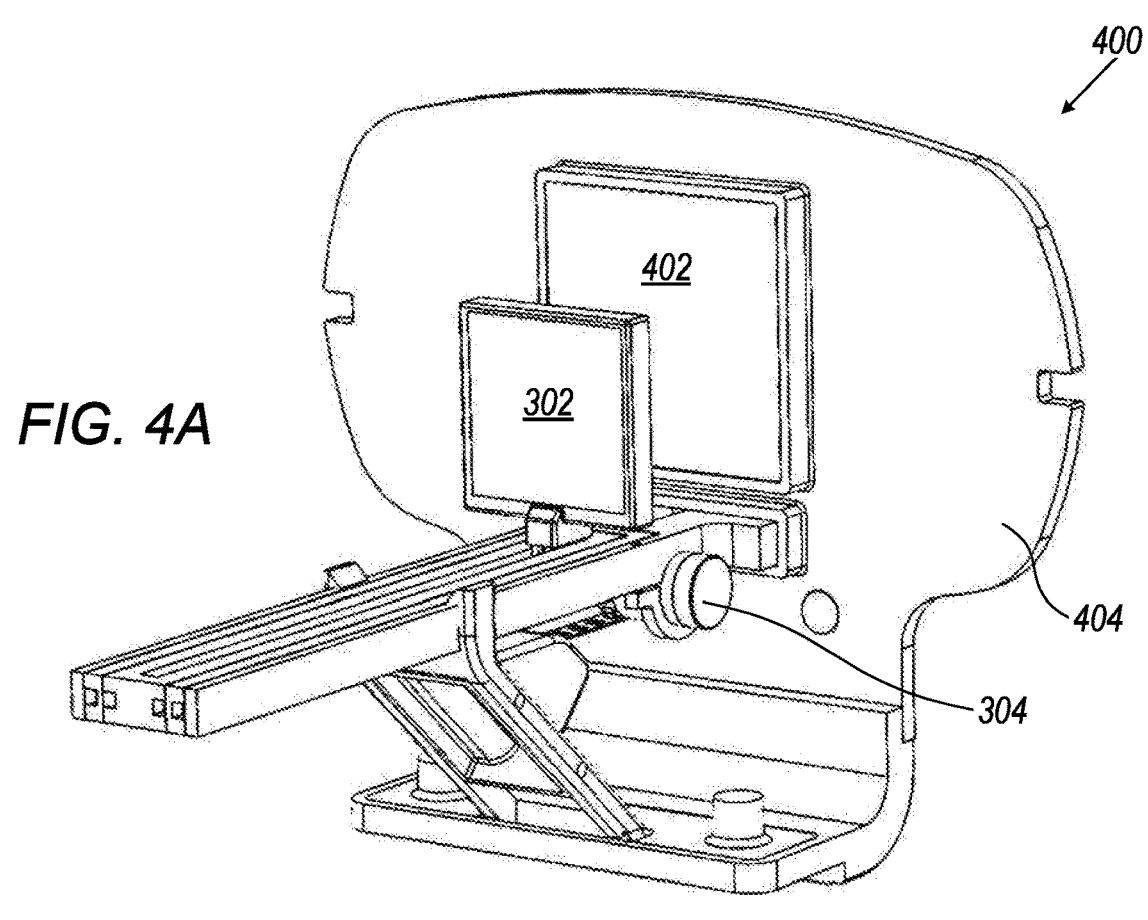
FIG. 4A is a simplified diagram of a first moveable screen on a rail and a second (rear) static screen of the system of FIG. 1A, in accordance with an embodiment of the present invention.

FIG. 4A shows the first moveable screen 302 on extendable telescopic 3-step rail element 310 and a second larger (rear) static screen 402 of the system of FIG. 1A, in accordance with an embodiment of the present invention. On the right side of the drawing, is seen a rear backing 404 of an outer casing 135 (FIG. 1A). The telescopic 3 steps rail is shown, and one 306 of the three said support is shown, and also shown a stepper motor.

Figure 4B:
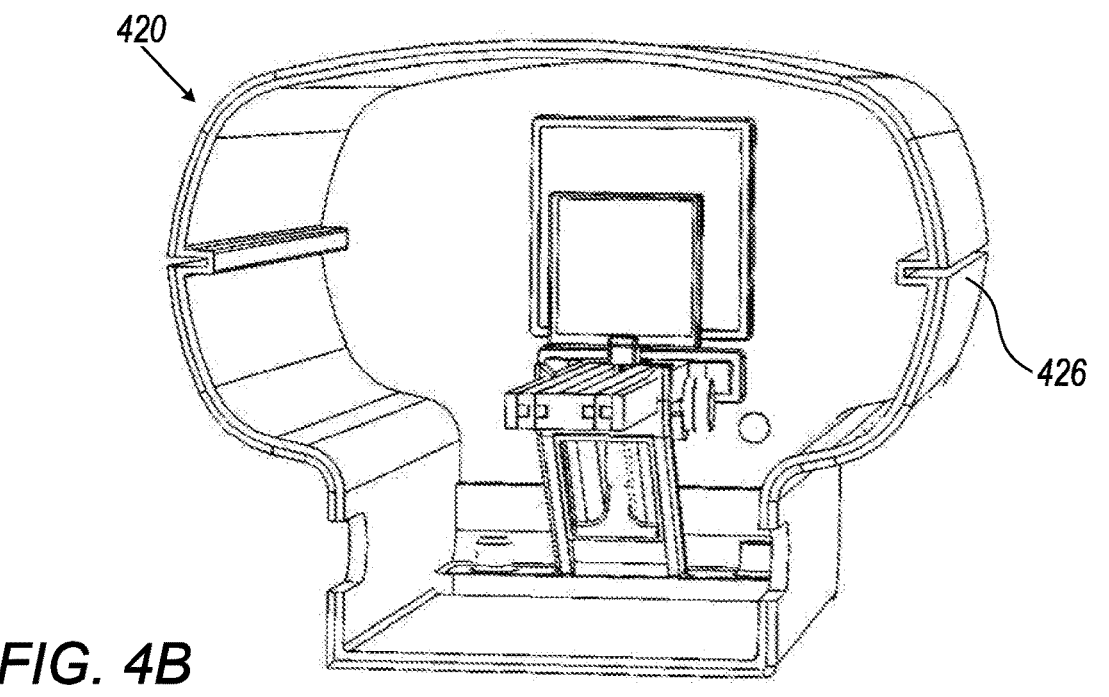
FIG. 4B is a simplified diagram of the casing of the screens of FIG. 4A, in accordance with an embodiment of the present invention.

FIG. 4B is a simplified diagram 420 of a casing 426 of the rear section, encasing the screens of FIG. 4A, in accordance with an embodiment of the present invention. In this figure, the two screens: the first front one 302 is movable but the second (rear) screen 402 is static. The screens are seen through a cutout view of the outer shell in its first section (in the rear section of the system).

Figures 5A, 5B, 5C:
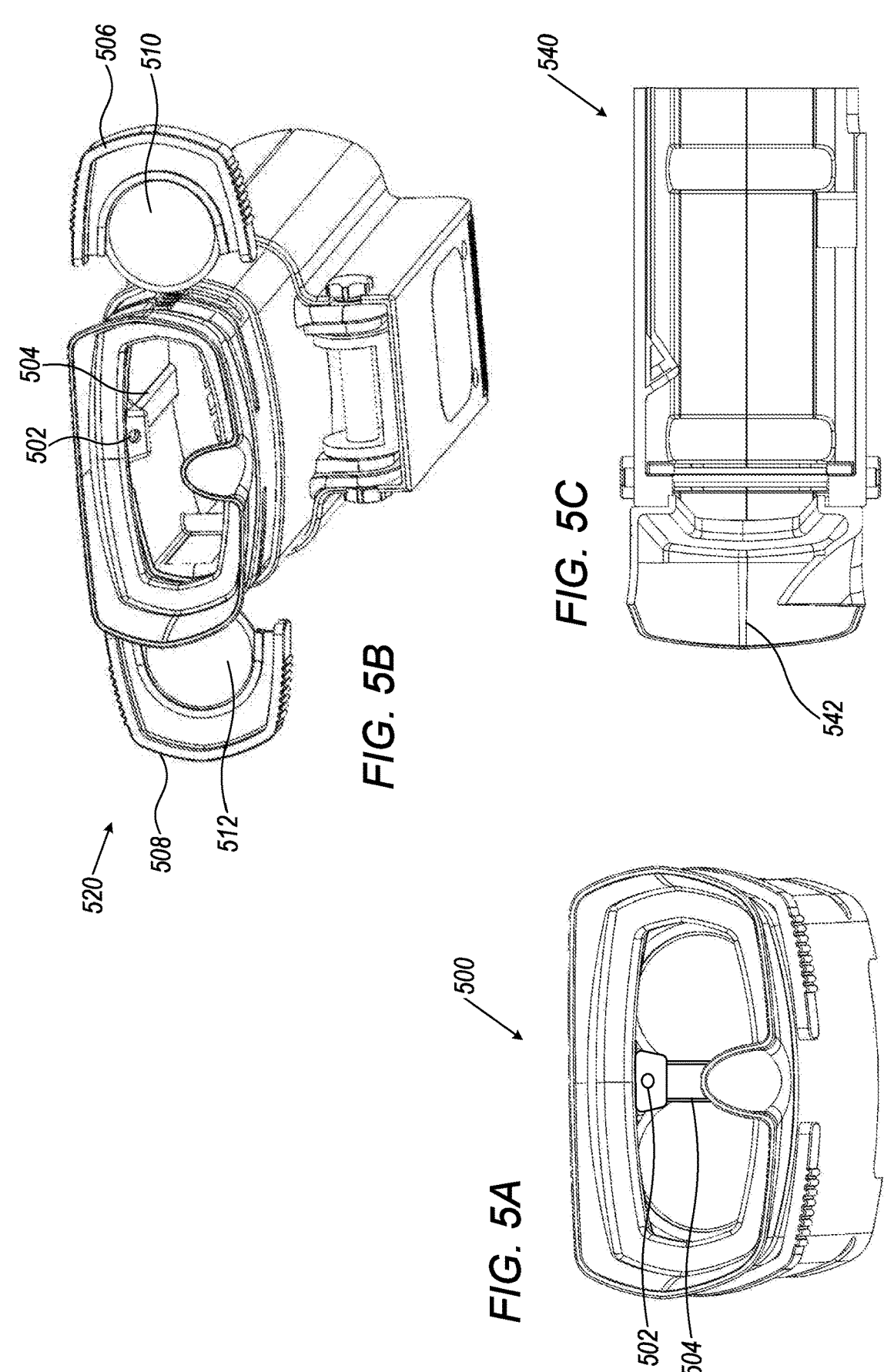
FIG. 5A is a simplified perspective diagram of an internal camera of the system of FIG. 1A, in accordance with an embodiment of the present invention.
FIG. 5B is a simplified perspective front view of an internal camera of the system of FIG. 1A, in accordance with an embodiment of the present invention.
FIG. 5C is a simplified perspective cross-section top view of an internal camera of the system of FIG. 1A, in accordance with an embodiment of the present invention.

FIG. 5A is a simplified perspective view 500 of the eyepiece section of the system of FIG. 1A, showing an internal camera 502 disposed distally to and centrally above the nose recess of the system of FIG. 1A, in accordance with an embodiment of the present invention. This internal camera acts as a gaze tracker of the user's eyes and supported by a movable arm 504, configured to move and hold the camera at a certain angle in front of the middle of a user's eyes, as shown.

FIG. 5B is a simplified perspective view 520 of the system of FIG. 1A, from below the right side, showing the internal camera 502, in accordance with an embodiment of the present invention; the camera is a gaze tracker camera, held on a support member 504, in front of the shown visor, and around the user is a rubber sealing member, for sealing the eyepiece section from light from outside the system and is in ergonomic form. Also seen, is a right side of dashed rail, for restraining opening and closing of the system. The system further comprises two lens holders 506 and 508, for holding two lenses 510, 512, respectively. The lens holders can be extended (as shown) or conveniently stored within the system, when not in use (retracted, not shown).

FIG. 5C is a simplified perspective cross-section top view 540 of an internal camera 502 of the system of FIG. 1A, in accordance with an embodiment of the present invention. This figure shows the location of the camera in front of the two eyes and in a symmetric distance from each eye. A virtual eye 542 is shown.

Figure 6A:
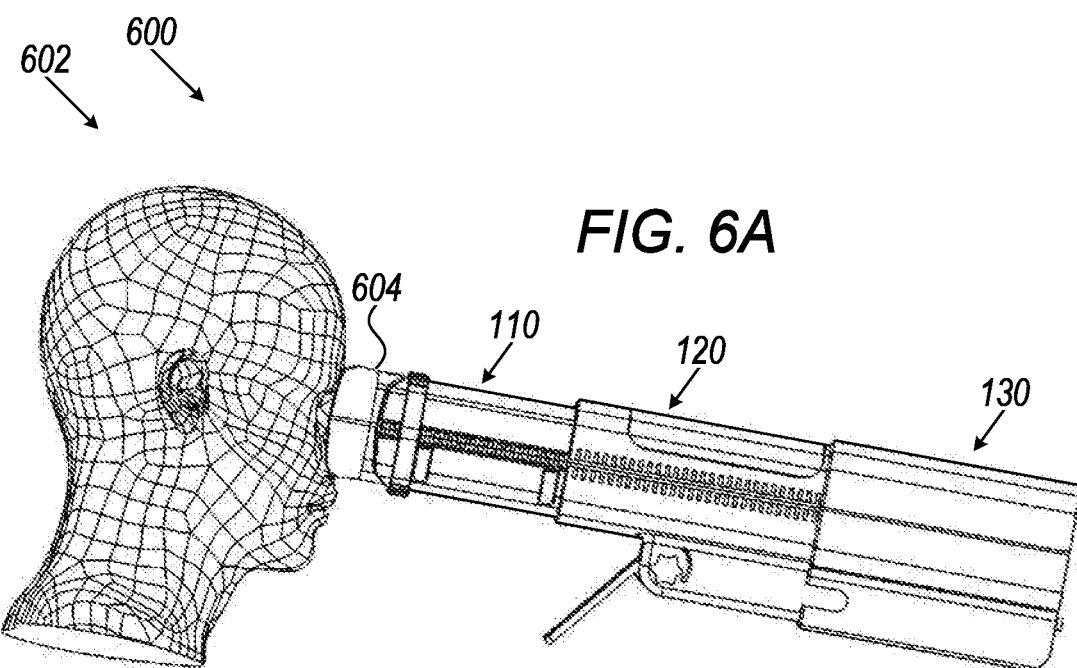
FIG. 6A is a simplified diagram of a side view of the open (extended) system of FIG. 1A, in accordance with an embodiment of the present invention.

FIG. 6A is a simplified diagram of a side view 600 of the open (extended) system 100 of FIG. 1A, in accordance with an embodiment of the present invention. A profile of a user's head 602 is seen with his eyes (not seen) placed proximally to an ergonomically-shaped shape visor 604, configured to seal the system from outside light. The dashed rail, also seen in in FIG. 5B is shown again, as is the adjustable front leg, and said knob for locking it in a selected angle for use.

Figure 6B:
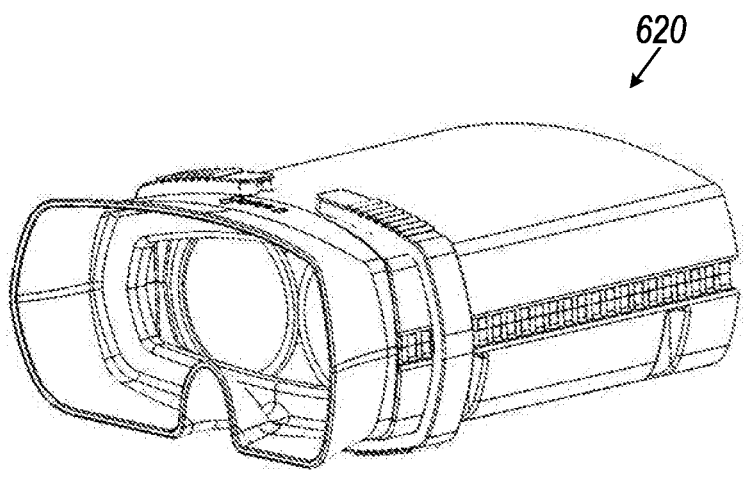
FIG. 6B is a simplified diagram of a perspective view of the third casing section of the system of FIG. 1A, in accordance with an embodiment of the present invention.

FIG. 6B is a simplified diagram of a perspective view 620 of the eyepiece section 110 of the system of FIG. 1A, in accordance with an embodiment of the present invention. This picture shows the frontal part of the system. The rubber forehead, ergonomically-shaped visor (shown) includes a location for the user's nose also shown in this figure. The dashed rail of said section is also shown in FIG. 6B.

Figure 7A:
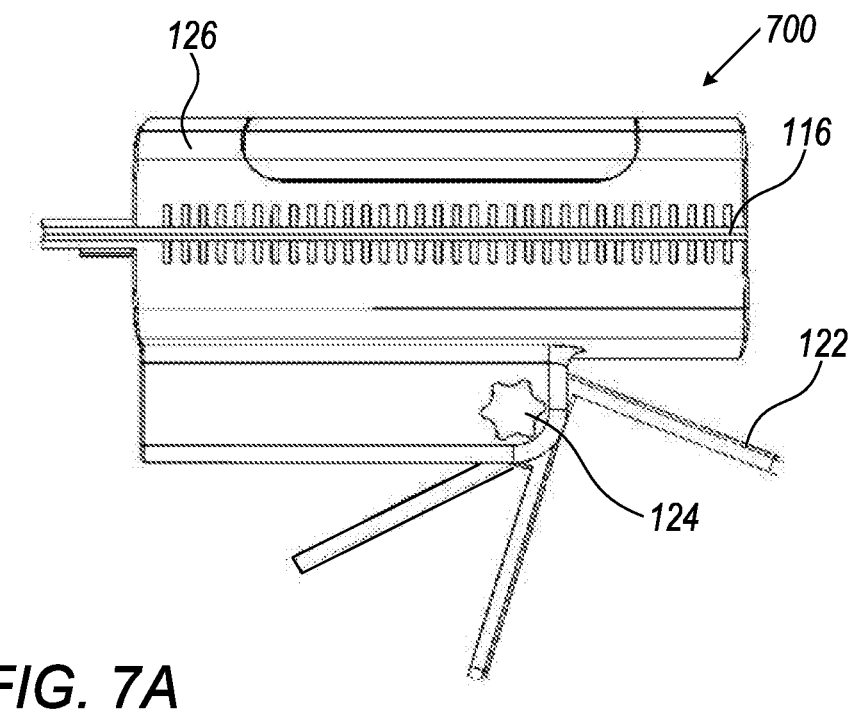
FIG. 7A is a simplified diagram of a side view of the second casing section of the system of FIG. 1A, in accordance with an embodiment of the present invention.

FIG. 7A is a simplified diagram of a side view 700 of the casing of the middle section 120 of system 100 of FIG. 1A, in accordance with an embodiment of the present invention. An adjustable stand 122 is shown and knob 122 for locking the stand in a selected angle for use. The dashed rail 116 is also shown in FIG. 7A.

Figure 7B:
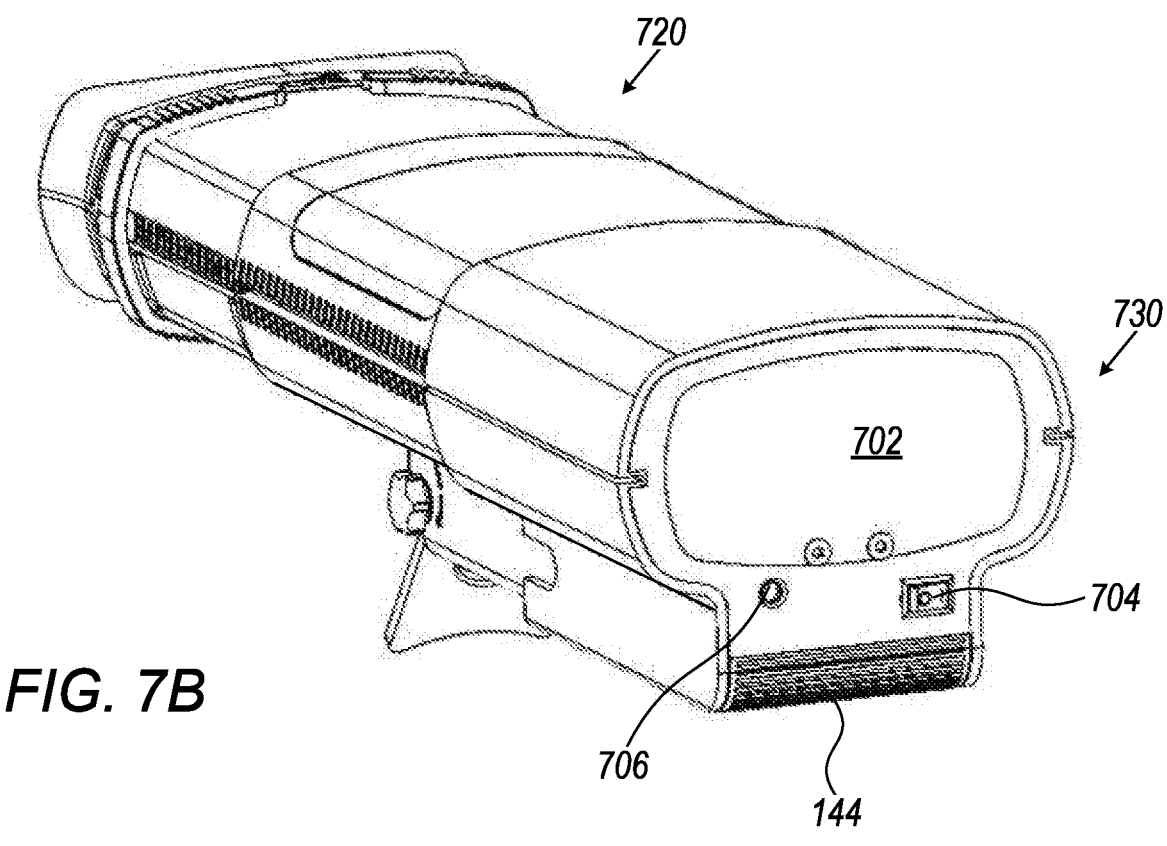
FIG. 7B is a simplified diagram of a rear view of the open (extended) system of FIG. 1A, in accordance with an embodiment of the present invention.

FIG. 7B is a simplified diagram of a rear view 720 of the open (extended) system 100 of FIG. 1A, in accordance with an embodiment of the present invention.

A flat rear surface 702 is seen for sticking an informative sticker, is shown at a rear end 730 of the system. Also shown in this figure in the rear the system, is a on/off power switch 704. A LED indicator light 706, and the rear, anti-slip element 144 (typically made of rubber/silicone).

Figure 8A:
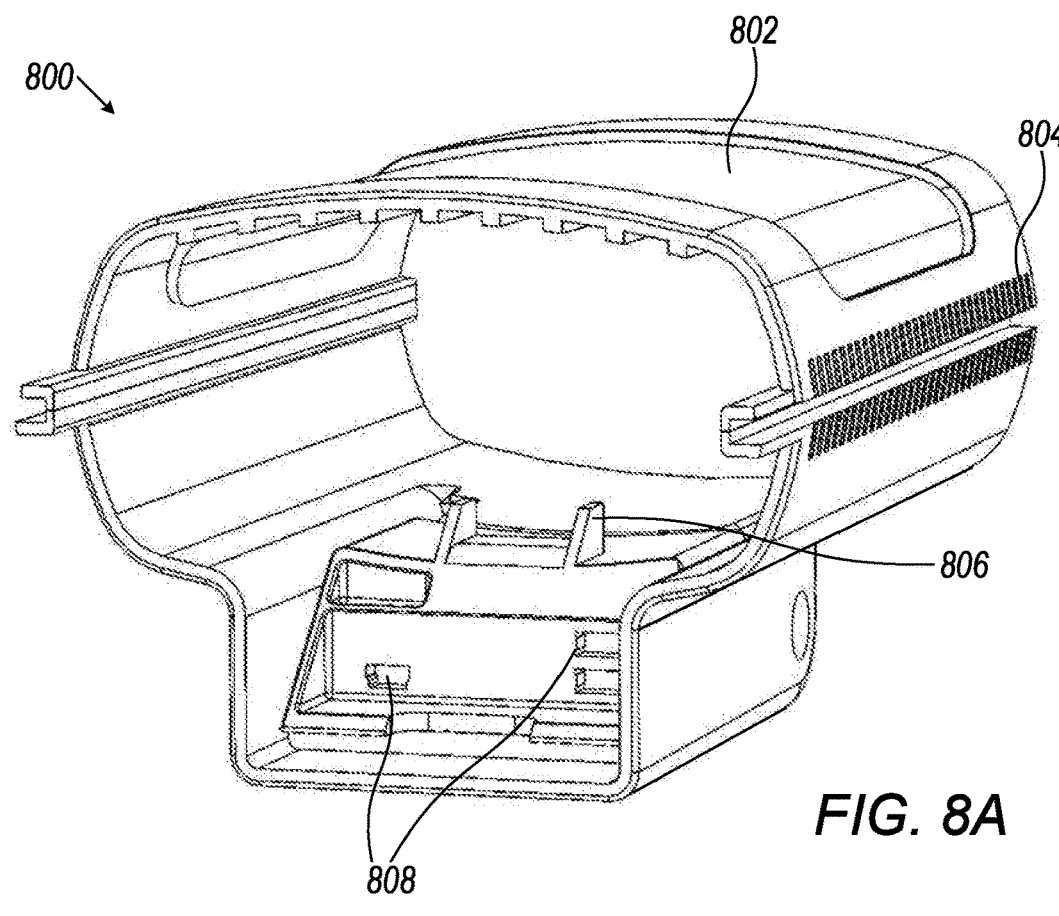
FIG. 8A is a simplified diagram of an inner perspective view of the second casing section of the system of FIG. 1A, in accordance with an embodiment of the present invention.

FIG. 8A is a simplified diagram of an inner perspective view of the middle (second) casing section 120 of system 100 of FIG. 1A, in accordance with an embodiment of the present invention. As shown, a dashed rail 804 is localized to restrain the horizontal opening and closing movement of the telescopic parts of the system. A middle section of rail support (of three) is shown. A receiving element 806 is shown for receiving the middle section rail element 310 (also called extendable telescopic 3-step rail element herein). This casing section also comprises a depressed outer silicone element 802. It also houses a microprocessor, computer or processor 808.

Figure 8B:
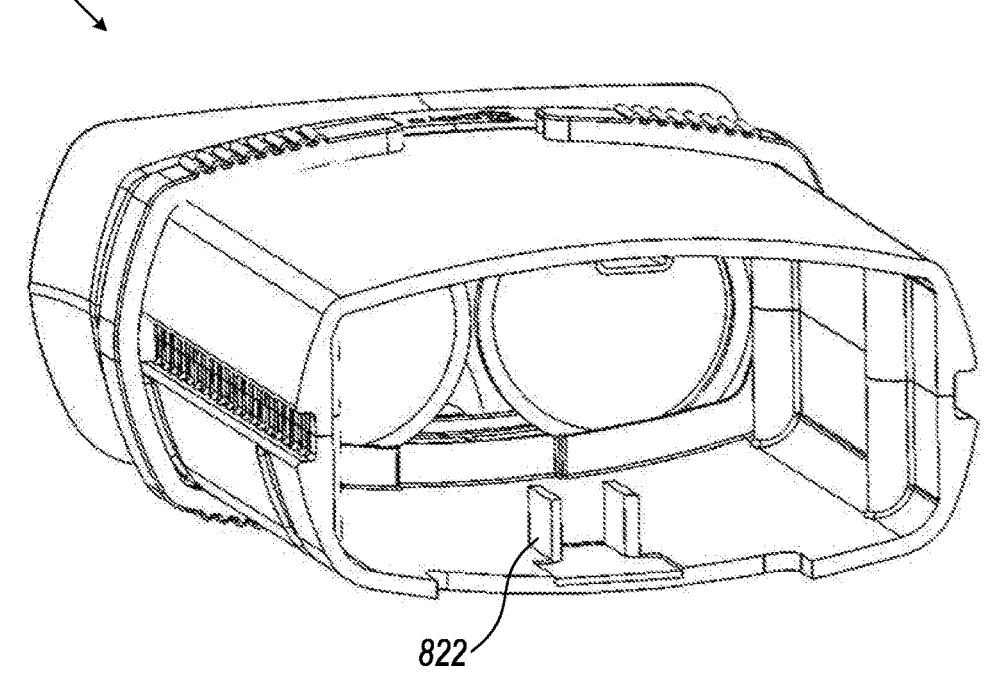
FIG. 8B is a simplified diagram of an inner perspective view of the rear section 120 (third casing section) of the system of FIG. 1A, in accordance with an embodiment of the present invention.

FIG. 8B is a simplified diagram of an inner perspective view 820 of the eyepiece casing section 110 of system 100 of FIG. 1A, in accordance with an embodiment of the present invention. A second receiving element 822 is seen for receiving a third section of the extendable telescopic 3-step rail element 310 of FIG. 3A, disposed to restrain the horizontal opening and closing move of the parts telescopic system.

FIG. 9 is a simplified schematic illustration showing a perspective front view 900 of an opened eyepiece (third) section 110 of the automated AI-controlled optical system 100 of FIG. 1A, in accordance with an embodiment of the present invention. In this view, an image 902 is seen on the front screen 302. The inner surfaces of the system are coated in black.

FIG. 10 is a simplified schematic illustration 1000 showing details of stepper motor 304 and an inner conveyor belt 1002 of the automated AI-controlled optical system of FIG. 1A, in accordance with an embodiment of the present invention. The stepper motor is in mechanical connection via a toothed wheel (or cogwheel) 1004, which connects perpendicularly with the conveyor belt. The conveyor belt comprises cut-outs 1006 along its length, the cut-outs being matched in size and longitudinal spacing to receive the teeth (or cogs) 1008 of the toothed/cog wheel.

Figure 11:
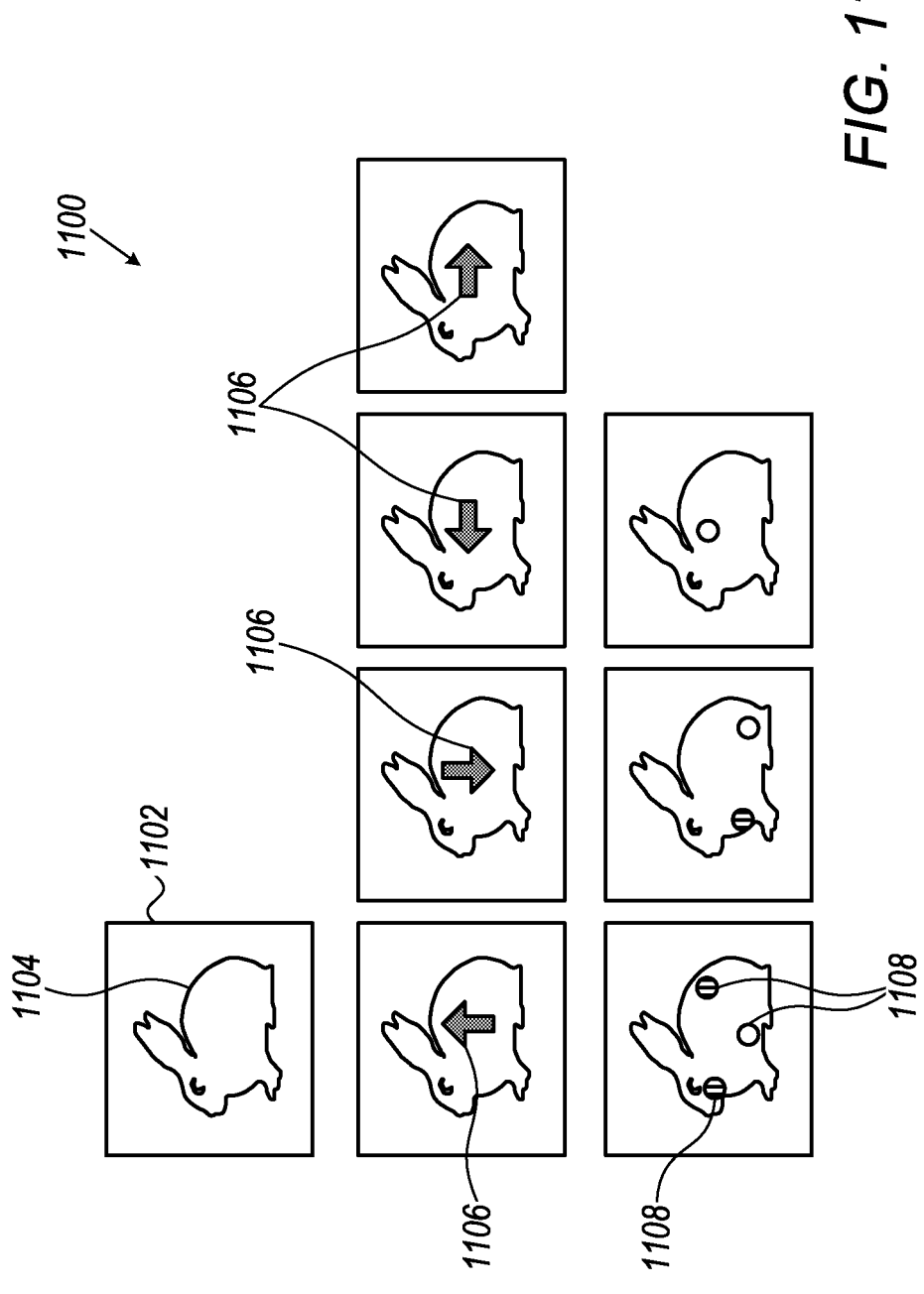
FIG. 11 is a set of images with superimposed symbols or instructions as appearing on a screen in the system of FIG. 1A, in accordance with an embodiment of the present invention.

FIG. 11 is a simplified illustration 1100 of an example of a set of images 1102 with superimposed symbols or instructions as appearing on a near (front) screen (302, FIG. 3A) in the system of FIG. 1A, in accordance with an embodiment of the present invention. In this illustration, in the top line is shown an example of a picture 1104 which can appear on screens 302, 402 (FIG. 4A). In the second line, arrows 1106 in four directions are shown, superimposed on the picture. May be other directions not shown; the direction of the arrows is showing in which direction the user is asked to move his eyes: to the right, to the left, up, down or other directions not shown. In the third line, are superimposed different sets of dots 1108, used also for testing and also for the treating the binocular vision.

Figure 12:
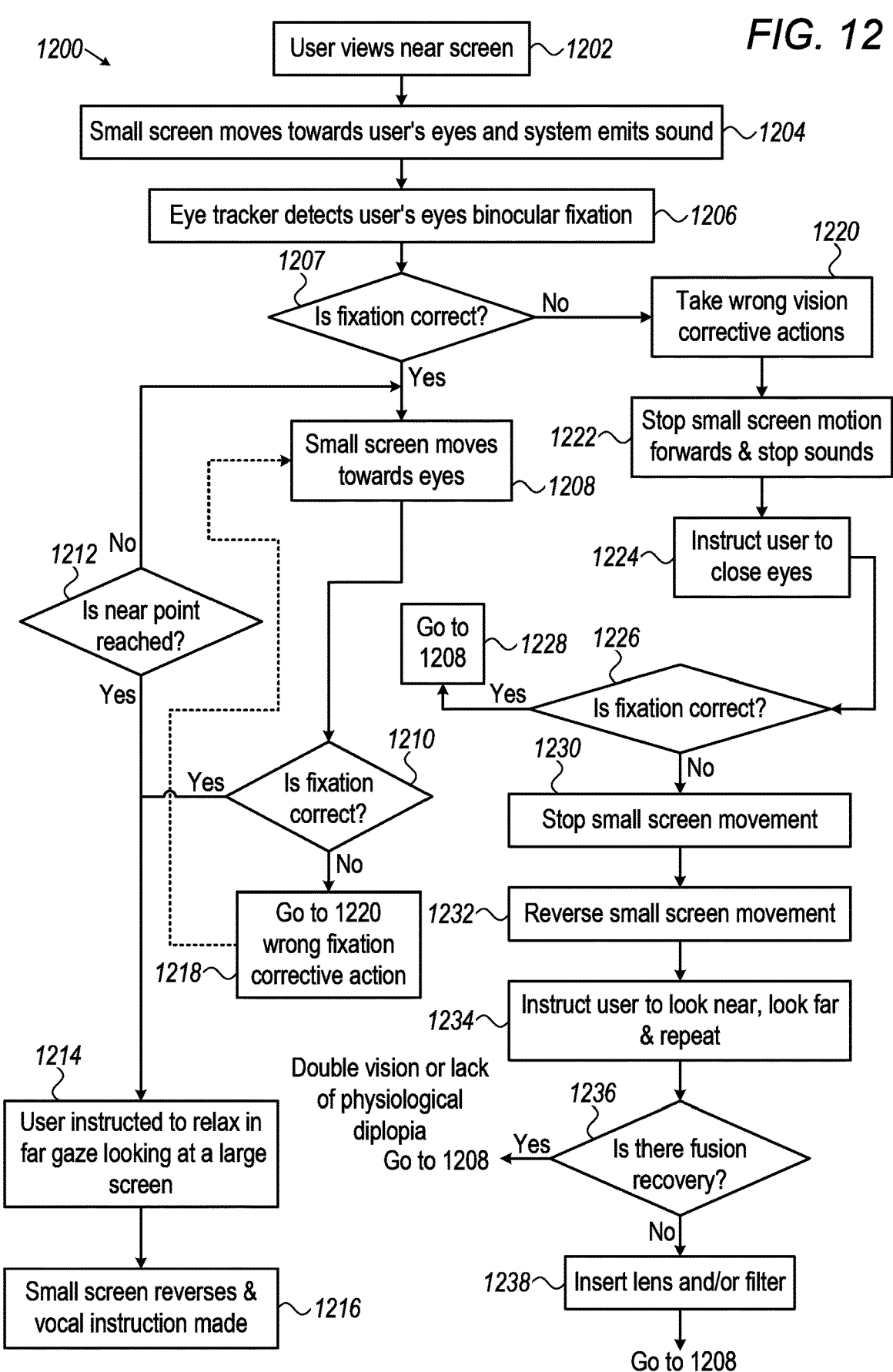
FIG. 12 is a simplified flowchart of an automated audio feedback computerized AI-controlled optical method for tracking eye exercises of a user, in accordance with an embodiment of the present invention.

Reference is now made to FIG. 12, which is a simplified flowchart 1200 of an automated audio feedback computerized AI-controlled optical method for tracking eye exercises of a user, in accordance with an embodiment of the present invention.

In a user viewing step 1202, the user views a near screen.

Thereafter, in a small screen moving step 1204, the small screen moves towards user's eyes and system emits a sound.

In an eye tracking step 1206, the eye tracker detects the user's binocular fixation.

In a first user's eyes fixation checking step 1207, the system checks to see if the user's eyes' fixation is correct.

If yes, then a second small screen moving step 1208 is performed, in which the small screen moves towards user's eyes.

In a second user's eyes fixation checking step 1210, the system checks to see if the user's eyes' fixation is correct.

If yes, a user's eyes' near point checking step 1212 is performed to check if the near point has been reached.

If no, the system resets to step 1208 and steps 1208-1212 are repeated.

If yes, then in a user instructing step 1214, the user instructed to relax in far gaze looking at large screen (far screen?).

Thereafter in a small screen reversing step 1216, the small screen reverses and vocal instructions to the user are made.

If the user has repeated steps 1208-1212 more than n times, and the outcome is negative, then a go to corrective action step 1218 is performed and the system is operative to continue with a wrong fixation corrective action step 1220.

In a take wrong fixation corrective action step 1220, the system is operative to review the user exercise history.

Typically, the system then performs a stop small screen motion forwards and stop sound step 1222.

In an instructing user step 1224, the system instructs the user to close his/her eyes.

In another user's eyes fixation checking step 1226, the system checks to see if the user's eyes' fixation is correct.

If yes, then the system is operative to perform a go to step 1228 and to go to step 1208.

If no, then the system performs a stop small screen movement step 1230, in which the movement of the small screen is stopped.

Thereafter, in a reverse small screen movement step 1232, the movement of the small screen is reversed.

In another user instruction step 1234, the system is operative to instruct user to look near and far and to repeat this.

In a user fusion recovery checking step 1236, the system is operative to check if there is user's eyes' fusion recovery. If yes, the system is operative to go to step 1208.

If no, the user/an operator inserts a lens or filter in an inserting lens and/or filter step 1238. Thereafter, the system is operative to go to step 1208.

The user performs eye exercises according to this method until an exercise session is completed—typically 20-60 minutes.

According to some embodiments of the present invention, the systems and apparatus described herein are used to treat convergence insufficiency in a patient. A non-limiting list of some of the common symptoms in convergence insufficiency appears in Table 1 herein below. These symptoms are monitored over the period of treatment of several months and can be used to define qualitative and/or quantitative improvements/changes during the treatment period.

13

TABLE 1

Common Symptoms in Convergence Insufficiency

| No. | Symptom |
| --- | --- |
| 1 | Occasional blurred vision |
| 2 | Headaches |
| 3 | Problems in reading |
| 4 | Eye fatigue |
| 5 | Blurred reading |
| 6 | Seeing double |
| 7 | Difficulty in focusing |
| 8 | Stabbing pains in eyes |
| 9 | Eye pain |
| 10 | Blinking |
| 11 | Occasional loss of tracking |
| 12 | Bright light blindness |
| 13 | Rubbing of eyes |
| 14 | Dizziness |
| 15 | Burning eyes |
| 16 | Heavy eyes |
| 17 | Tear drops |
| 18 | Eyes pressure feeling |
| 19 | Problems in writing down from black/whiteboard |
| 20 | Lack of control of eye closure |
| 21 | Does not get used to reading glasses |
| 22 | General fatigue |
| 23 | Closes one eye when reading |
| 24 | Red eyes |
| 25 | Holds head in slanted position |
| 26 | Other, such as difficulties at school and difficulties on a computer |

According to some further embodiments of the present invention, the systems and apparatus described herein are used to treat for eye training in a patient. There are several accessories, which are used in a number of different stages. One non-limiting example appears in Table 2 herein below.

The systems of the present invention may be built to any suitable size and dimensions, such as 30 cm x 30 cm×70 cm. These exemplary dimensions should not be deemed limiting.

It should also be understood that the systems of the present invention may be activated by guests and host users in combinations other than those described herein.

TABLE 2

Stages of Eye training and use of accessories therein.

| STAGE NUMBER | LENSES | COLOR FILTER* | LIGHTS |
| --- | --- | --- | --- |
| STAGE ONE | −3 LENSES | +COLOR FILTER | +LIGHTS |
| STAGE TWO | −3 LENSES | NO COLOR FILTER | +LIGHTS |
| STAGE THREE | NO LENSES | NO COLOR FILTER | +LIGHTS |
| STAGE FOUR | NO LENSES | NO COLOR FILTER | NO LIGHTS |
| STAGE FIVE | +3 LENSES or addition of base-out prism | NO COLOR FILTER | NO LIGHTS |

*According to some embodiments, color filters may be replaced by Polaroid lenses. On the other hand, in some occurrences of 3D tests, Polaroid lenses or color filters are not required.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. An automated, standalone, audio-feedback Artificial Intelligence-controlled optical system for tracking eye exercises of a patient, the system comprising:

an eye piece section;

a middle section;

a rear section, the sections being nestable in a telescopic manner, an extendable telescopic 3-step rail element including an extension rail mechanism, comprising:

a rear rail element, a middle rail element, an eyepiece rail element, wherein the middle rail element is nested in the rear rail element and the eyepiece rail element is nested in the middle rail element, a metallic spring belt used to extend or retract the extendable telescopic 3-step rail element, and a first movable screen movable along the extendable telescopic 3-step rail element, wherein the telescopic sections are adapted to house a) an Artificial Intelligence-controlled optical tracking device adapted to continuously, automatically, track eye exercises of a patient, b) a user-activated apparatus for performing eye exercises of both eyes together, and)

c) a processor adapted to receive data from the Artificial Intelligence-controlled eye tracking device and from the user-activated apparatus thereby providing the user with eye exercises for improving user eye function over time.

2. An automated audio-feedback Artificial Intelligence-controlled optical system according to claim 1, further comprising an electronic apparatus adapted to download the data to a memory in the system.

3. An automated audio-feedback Artificial Intelligence-controlled optical system according to claim 1, further comprising software readable by the processor, wherein the software is adapted to form user records over time.

4. An automated Artificial Intelligence-controlled optical system according to claim 1, wherein the optical tracking device comprises a camera.

5. An automated AI controlled Artificial Intelligence-controlled optical system according to claim 1, wherein the optical tracking device comprises a video camera.

6. An automated AI controlled Artificial Intelligence-controlled optical system according to claim 5, wherein the camera is adapted to capture images of each the users eyes continuously or semi-continuously.

7. An automated Artificial Intelligence-controlled optical system according to claim 3, wherein the software is adapted to output user records to an external computer system.

8. An automated Artificial Intelligence-controlled optical system according to claim 1, wherein the system is constructed and configured to improve eye fusion deficiencies of the patient over time.

9. An automated Artificial Intelligence-controlled optical system according to claim 8, wherein the fusion deficiencies, are selected from convergence insufficiency, divergence excess, intermittent strabismus and combinations thereof.

10. An automated Artificial Intelligence-controlled optical system according to claim 9, wherein the convergence insufficiencies is exophoria.

11. An automated Artificial Intelligence-controlled optical system according to claim 9, wherein the intermittent strabismus is intermittent exotropia.

12. An automated Artificial Intelligence-controlled optical system according to claim 1, wherein the user-activated apparatus comprises:

a. an ocular apparatus comprising:

i. at least one viewing aperture, disposed in front of the patient's eyes;

ii. the viewing aperture adapted to receive at least one of:

a. an optical lens;

b. an optical filter; and c. a prismatic lens.

13. An automated Artificial Intelligence-controlled optical system according to claim 12, wherein the user-activated apparatus further comprises:

a second screen arranged at a rear backing of the rear section; and a carrier element adapted to carry at least one of the first screen and the second screen towards and away from the ocular apparatus.

14. An automated AI controlled Artificial Intelligence-controlled optical system according to claim 13, wherein the two screens display at least one of a picture, a photo, an alphanumeric symbol and at least one colored shape.

15. An automated Artificial Intelligence-controlled optical system according to claim 12, wherein the user-activated apparatus further comprises at least one electrical light element attached to the carrier element.

16. An automated Artificial Intelligence-controlled optical system according to claim 12, wherein the user-activated apparatus further comprises an audio feedback element for generating, during the eye exercises, an audio signal whose characteristics are indicative of a distance of one of the at least two screens from the at least one viewing aperture.

17. An automated Artificial Intelligence-controlled optical system according to claim 12, wherein the carrier element further comprises a distance adjusting element adapted to position the at least two screens and the lamp means each at an equal distance from the at least one viewing aperture.

18. An automated Artificial Intelligence-controlled optical system according to claim 1, further comprising a remote controlled motor for moving at least one of the two screens towards the at least one viewing apertures.

19. An automated Artificial Intelligence-controlled optical system according to claim 17, wherein the audio feedback signal characteristics include its frequency.

20. An automated Artificial Intelligence-controlled optical system according to claim 19, wherein the audio feedback signal includes pulses and the signal characteristics include its pulse repetition rate.

* * * * *